(12) United States Patent
Ikeguchi

(10) Patent No.: US 6,699,216 B2
(45) Date of Patent: Mar. 2, 2004

(54) METHOD OF INDUCING NEGATIVE PRESSURE IN THE URINARY COLLECTING SYSTEM AND APPARATUS THEREFOR

(75) Inventor: Edward F. Ikeguchi, Larchmont, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/288,605

(22) Filed: Nov. 5, 2002

(65) Prior Publication Data

US 2003/0060806 A1 Mar. 27, 2003

Related U.S. Application Data

(62) Division of application No. 09/048,448, filed on Mar. 26, 1998, now Pat. No. 6,500,158.
(60) Provisional application No. 60/041,701, filed on Mar. 26, 1997.

(51) Int. Cl.[7] ............................................. A61M 29/00
(52) U.S. Cl. ................... 604/96.01; 604/523; 604/544; 604/319
(58) Field of Search .................... 604/93.01, 176, 604/544, 73, 540, 174, 523, 264, 319, 96, 98, 97, 79, 196, 48

(56) References Cited

U.S. PATENT DOCUMENTS

| | | |
|---|---|---|
| 1,828,986 A | 10/1931 | Stevens |
| 2,212,334 A | 8/1940 | Wallerich |
| 2,944,551 A | 7/1960 | Breer |
| 3,435,827 A | 4/1969 | Ericson |
| 3,807,408 A | 4/1974 | Summers |
| 3,938,530 A | 2/1976 | Santomieri |
| 3,943,929 A | 3/1976 | Patel |
| 3,988,782 A | 11/1976 | Dardik et al. |
| 4,084,589 A * | 4/1978 | Kulvi ........................... 604/73 |
| 4,084,593 A * | 4/1978 | Jarund ......................... 604/27 |
| 4,469,100 A | 9/1984 | Hardwick |
| 4,531,939 A | 7/1985 | Izumi |
| 4,820,270 A | 4/1989 | Hardcastle et al. |
| 4,990,137 A * | 2/1991 | Graham ........................ 604/73 |
| 5,053,009 A | 10/1991 | Herzberg |
| 5,356,382 A | 10/1994 | Picha et al. |
| 5,499,994 A | 3/1996 | Tihon et al. |
| 5,520,636 A | 5/1996 | Korth et al. |
| 5,536,240 A | 7/1996 | Edwards et al. |
| 5,558,642 A | 9/1996 | Schweich, Jr. et al. |
| 5,569,219 A | 10/1996 | Hakki et al. |
| 5,624,395 A | 4/1997 | Mikhail et al. |
| 5,785,685 A * | 7/1998 | Kugler et al. ............. 604/99.03 |
| 5,800,392 A | 9/1998 | Racchini |
| 5,904,701 A | 5/1999 | Daneshvar |
| 5,913,814 A * | 6/1999 | Zantos ........................ 600/18 |
| 5,989,230 A * | 11/1999 | Frassica ...................... 604/264 |
| 6,080,142 A * | 6/2000 | Sachse ........................ 604/544 |
| 6,179,815 B1 * | 1/2001 | Foote ......................... 604/181 |
| 6,245,008 B1 * | 6/2001 | Leschinsky et al. .......... 600/18 |
| 6,364,868 B1 * | 4/2002 | Ikeguchi ...................... 604/514 |
| 6,500,158 B1 * | 12/2002 | Ikeguchi ...................... 604/319 |

OTHER PUBLICATIONS

Coe, "Alterations in Urinary Function and Electrolytes," Harrison's Principle of Internal Medicine, 13th Ed., pp. 235–262, McGraw–Hill, 1994.

* cited by examiner

Primary Examiner—Weilun Lo
Assistant Examiner—Michael G. Bogart
(74) Attorney, Agent, or Firm—William H. Dippert; Reed Smith LLP

(57) ABSTRACT

This invention concerns a method of improving kidney function, whereby a negative pressure is induced in the kidney. One embodiment useful in this regard comprises a balloon catheter having at least one lumen therethrough where the proximal end of the lumen is connected to a vacuum source.

5 Claims, 3 Drawing Sheets

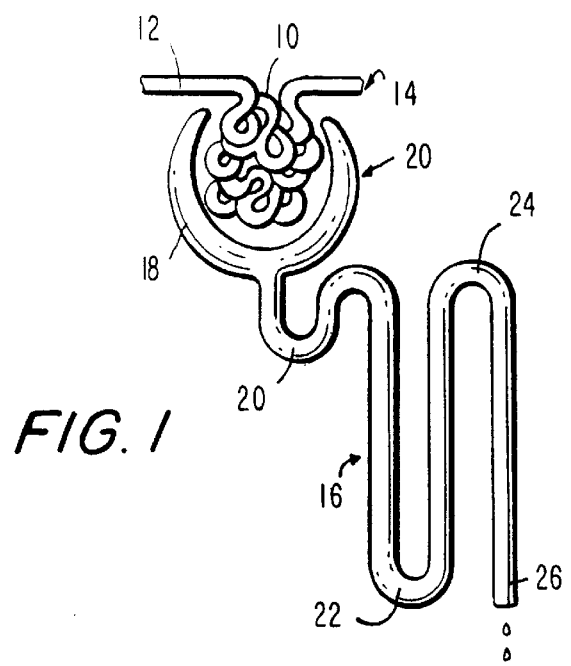
FIG. 1
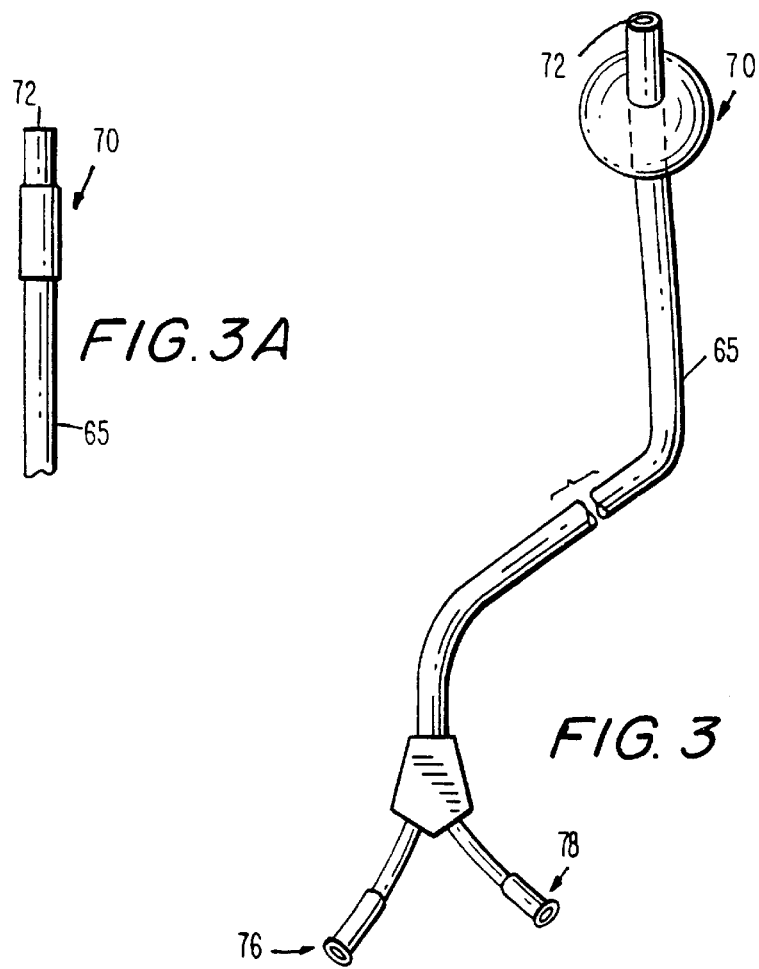
FIG. 3A
FIG. 3

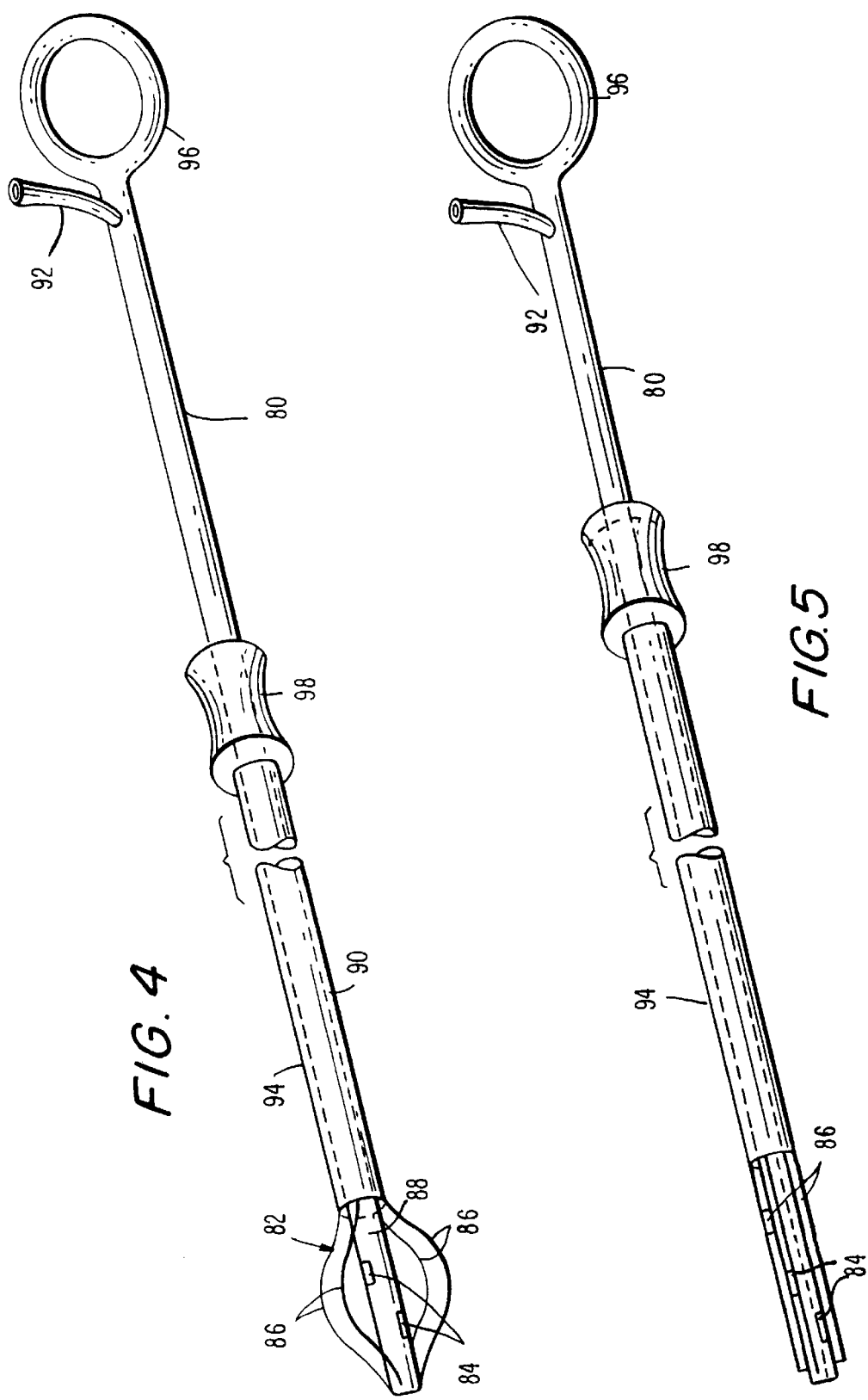

METHOD OF INDUCING NEGATIVE PRESSURE IN THE URINARY COLLECTING SYSTEM AND APPARATUS THEREFOR

CROSS-REFERENCE TO RELATED APPLICATIONS

This application is a divisional of co-pending U.S. Patent Application Ser. No. 09/048,448, filed Mar. 26, 1998, now U.S. Pat. No. 6,500,158, issued Dec. 31, 2002 which in turn claims the benefit of U.S. Provisional Patent Application Ser. No. 60/041,071, filed Mar. 26, 1997.

FIELD OF THE INVENTION

This invention relates to a method of improving kidney function. More specifically, this invention relates to a method of improving the hydrostatic forces and hemodynamics of the kidney through the manipulation of pressures within the urinary collecting system.

BACKGROUND OF THE INVENTION

A fundamental understanding of renal physiology can be readily found in the available medical literature, such as "Section 6: Alterations in Urinary Function and Electrolytes", *Harrison's Principle of Internal Medicine*, McGraw-Hill, 1994, 13th ed., p. 235–262. The main function of the kidneys is to maintain the constancy of the body's internal environment by regulating the volume and composition of the extracellular fluids. To accomplish this, the kidneys balance precisely the intake, production, excretion, and consumption of many organic and inorganic compounds. This balancing requires that the kidneys perform several more specific functions.

One of the specific functions of the kidneys is the excretion of inorganic compounds. The renal excretion of sodium ion ($Na^+$), potassium ion ($K^+$), calcium ion ($Ca^{++}$), magnesium ion ($Mg^{++}$), hydrogen ion ($H^+$), and bicarbonate ion ($HCO3^-$) exactly balances the intake and excretion of these substances through other routes, for example, the gastrointestinal tract and the skin.

Another specific function of the kidneys is the excretion of organic waste products. Normally the kidneys excrete such waste products as urea and creatinine in amounts that equal their rate of production.

A third specific function of the kidneys is the regulation of blood pressure through the formation and release of renin. Renin is a major component of the renin-angiotensinaldosterone mechanism which directly affects the tension in the walls of arteries. In addition, the renin-angiotensinaldosterone mechanism also controls blood pressure by controlling body fluid volume.

A fourth function of the kidneys is the regulation of the production of erythrocytes through the formation and release of renal erythropoietic factor.

Finally, the last specific kidney function is the activation of Vitamin D. Vitamin D which is ingested must undergo two activation steps in the body before it can regulate calcium metabolism. The first activation step occurs in the liver, and the second occurs in the kidney.

An understanding of renal physiology requires familiarity with the anatomy of the kidney. The kidneys are located retroperitoneally in the upper dorsal region of the abdominal cavity and have bean-like shapes, as shown in FIG. 2. The concave curve or innermost part is called the renal pelvis, while the convex curve or outermost part is called the renal cortex. Between the cortex and the pelvis lies the renal medulla. The artery supplying the kidney is the renal artery, and the vein draining the kidney is the renal vein. The ureter, which drains the kidney of water, mineral and wastes, empties into the bladder, which in turn empties through the urethra. The renal artery, renal vein and ureter attach to the kidney at the renal pelvis.

On a microscopic level, each kidney is made up of approximately one million smaller units called nephrons. This basic functional unit of the kidney, as shown in FIG. 1, is composed of a glomerulus 10 with its associated afferent 12 (i.e., entering) and efferent 14 (i.e., exiting) arterioles and a renal tubule 16. The glomerulus 10 consists of a tuft of 20–40 capillary loops protruding into Bowman's capsule 18, a cup-like shaped extension of the renal tubule which is the beginning of the renal tubule. The epithelial layer of Bowman's capsule 18 is only about 400 Å thick, which facilitates passage of water and inorganic and organic compounds. In addition, the capillary endothelium is fenestrated (i.e., porous) with an incomplete basement membrane which further facilitates passage of water and inorganic and organic compounds. The renal tubule has several distinct regions which have different functions: the proximal convoluted tubule 20, the loop of Henle 22, the distal convoluted tubule 24, and the collecting duct 26 that carries the final urine to the renal pelvis and the ureter.

There are two basic types of nephrons, cortical nephrons and juxtamedullary nephrons. The cortical nephrons comprise about 85% of all nephrons in the kidney and have glomeruli located in the renal cortex. In addition, cortical nephrons have short loops of Henle which descend only as far as the outer layer of the renal medulla. The juxtamedullary nephrons are located at the junction of the cortex and the medulla of the kidney. Juxtamedullary nephrons have long loops of Henle, which penetrate deep into the medulla and sometimes reach the tip of the renal papillae. These nephrons are important in the counter-current system, by which the kidneys concentrate urine.

The constancy of the body's internal environment is maintained, in large part, by the continuous functioning of its roughly two million nephrons. As blood passes through the kidneys, the nephrons clear the plasma of unwanted substances (e.g., urea) while simultaneously retaining other, essential substances (e.g., water). Unwanted substances are removed by glomerular filtration and renal tubular secretion and are passed into the urine. Substances that the body needs are retained by renal tubular secretion and are returned to the bloody by reabsorptive processes.

Glomerular filtration, i.e., the amount of fluid movement from the capillaries into Bowman's capsule, is the initial step in urine formation. The plasma that traverses the glomerular capillaries is filtered by the highly permeable glomerular membrane, and the resultant fluid, the glomerular filtrate, is passed into Bowman's capsule. Glomerular filtration rate (GFR) refers to the volume of glomerular filtrate formed each minute by all of the nephrons in both kidneys. The glomerular filtrate then passes along the renal tubule and is subject to the forces in the proximal convoluted tubule, the loop of Henle, the distal convoluted tubule and finally the collecting duct. The renal tubule functions either to secrete or reabsorb organic or inorganic compounds into or from the glomerular filtrate. Both of these renal tubular functions involve active transport mechanisms as opposed to passive transport mechanisms.

Glomerular filtration is proportional to the membrane permeability and to the balance between hydrostatic and oncotic forces. The hydrostatic pressure driving glomerular filtration is the gradient between intrarenal blood pressure and the pressure within the Bowman's capsule (presumed to be approximately atmospheric). The intrarenal pressure is for all intents and purposes equivalent to the systolic and diastolic blood pressures measured peripherally. Since the intrarenal blood pressure in all living beings is greater than atmospheric pressure, the hydrostatic pressure can be conceptualized as the pressure driving fluid out of the glomerular capillary and into Bowman's capsule. The colloid oncotic pressure gradient is the difference between the concentrations of particles on either side of a water permeable membrane through which the particles cannot pass. Since there are many particles within the capillaries that cannot pass through the capillary endothelium including cells, platelet, and macromolecules, the colloid oncotic pressure gradient can be conceptualized as the pressure driving fluid into the glomerular capillary. When the hydrostatic pressure exceeds the oncotic pressure, filtration occurs. Conversely, when the oncotic pressure exceeds the hydrostatic pressure, reabsorption occurs.

In the body, the major determinant of GFR is the hydrostatic pressure within the glomerulus. In addition, the renal blood flow (RBF) through the glomeruli has a great effect on GFR; when the rate of RBF increases, so does GFR. There are several factors which control the RBF: (1) an intrinsic phenomenon observed in the renal capillaries called autoregulation, (2) sympathetic stimulation through the autonomic nervous system, and (3) arteriolar resistance.

The term "kidney function" or "renal function" generally refers to the kidneys' ability to clear creatinine. Creatinine clearance normally declines with age, as does GFR. Thus, kidney function is generally synonymous with GFR. The decline in GFR with age is due to declines in renal plasma flow, cardiac output, and renal tissue mass.

Renal failure is divided into two main categories: (1) acute renal failure and (2) chronic renal failure. Acute renal failure (ARF) is the clinical condition associated with rapid, steadily increasing azotemia (elevated level of blood urea nitrogen (BUN)), with or without oliguria (<500 mL/day of urine output). Chronic renal failure (CRF) is the clinical condition resulting from a multitude of pathologic processes that lead to derangement and insufficiency of renal excretory and regulatory function (uremia).

ARF is further subdivided into three diagnostic categories: (1) prerenal azotemia, which is due to inadequate renal blood perfusion, (2) renal azotemia, which is due to diseases or abnormal conditions within the kidney itself, and (3) postrenal azotemia, which is due to obstruction of kidney outflow either at the point of the ureters, the bladder or the urethra.

A great deal of research has focused on the effects of postrenal obstruction on renal hemodynamics, metabolism, and filtration/concentrating ability, perhaps because postrenal obstruction is a rather common clinical condition. Diseases which cause postrenal obstruction include: (1) kidney and ureteral stones, (2) cancers of the ureter, bladder, or prostate, and (3) congenital anomalies such as posterior urethral valves. In all of these disease entities, the common pathologic process is an obstruction to the flow of urine with a subsequent rise in pressure in the collecting system. It is well known that when this occurs, renal blood flow is diminished, renal blood flow is redistributed from cortex to medulla, glomerular filtration decreases, and tubular concentrating ability fails. However, there is no known research conducted or reported on the effects of negative pressure applied to the renal collecting system with respect to renal physiology and the parameters mentioned above.

Because, anatomically, the kidney is one of the few areas of the body where the intravascular space is in direct extension with the external atmosphere (i.e., the vascular endothelium of the glomerulus is porous and in direct contact with the Bowman's capsule and tubules of the nephron which connect to the ureter, bladder, and ultimately the outside world via the urethra), the physiology of the kidney can be altered by changing the atmospheric pressure. It is therefore desirable to reduce the pressure at the outflow tract of the urinary system, i.e., the renal collecting system, below atmospheric pressure, which would then be transmitted to the level of the Bowman's capsule to increase hydrostatic pressure and thereby increase glomerular filtration and kidney function.

Experimentation has been conducted in a swine model to confirm this hemodynamic affect of negative pressure on the collecting system of the kidney. Under direct vision with the kidney exposed, the venal collecting system was brought to −40 cm $H_2O$ pressure in four otherwise healthy pigs. Average blood pressure was found to fall by 16 mm Hg systolic and 12 mm Hg diastolic. Heart rate rose by an average of 14 bpm.

Although it is conceivable that a single-lumen conventional ureteral catheter could be used for this purpose, there are several problems which would likely arise. Most importantly, once the lumenal portion of a ureteral catheter is positioned in the renal pelvis and suction is applied to this catheter, the drainage holes of the catheter may become occluded if they are sucked up against the mucosa of the renal pelvis. This would interfere with the negative pressure applied to the ureteral catheter from transmitting to the level of the glomerulus.

OBJECTS OF THE INVENTION

It is an object of the invention to provide a method of improving kidney function.

It is also an object of the invention to provide a method of improving the hydrostatic forces and hemodynamics of the kidney through manipulation of pressures within the urinary collecting system.

It is a further object of the invention to provide a ureteral catheter with a retractable cage apparatus which would prevent the suction and entrapment of the urinary collecting system mucosa in its drainage holes.

These and other objects of the invention will become more apparent from the description below.

SUMMARY OF THE INVENTION

The present invention is directed to a method of increasing kidney function by reducing the pressure of the urinary outflow tract. The present invention is further directed to a method of treating renal failure caused by renal disease or urinary outflow obstruction by reducing the pressure of the urinary outflow tract. The present invention is also directed to an apparatus which is used to reduce the pressure of the urinary outflow tract and to a method of increasing kidney function by reducing the pressure of the urinary outflow tract in conjunction with a drug that increases renal blood flow. Lastly, the present invention is directed to a kit which is portable and convenient and which reduces the pressure at the urinary outflow tract to increase kidney function.

BRIEF DESCRIPTION OF THE DRAWINGS

FIG. 1 is a microscopic representation of the normal anatomy of the nephron, which is the basic renal unit involved in the production of urine;

FIG. 3 is a perspective view of a ureteral catheter useful according to the invention;

FIG. 3A is a perspective view of the distal portion of the catheter of FIG. 3, with the balloon uninflated;

FIG. 4 is a partly cross-sectional view of a catheter useful according to the invention, with the distal portion open; and FIG. 5 is a partly cross-sectional view of the catheter of FIG. 4 with the distal portion closed.

DETAILED DESCRIPTION OF THE INVENTION

Figure 2:
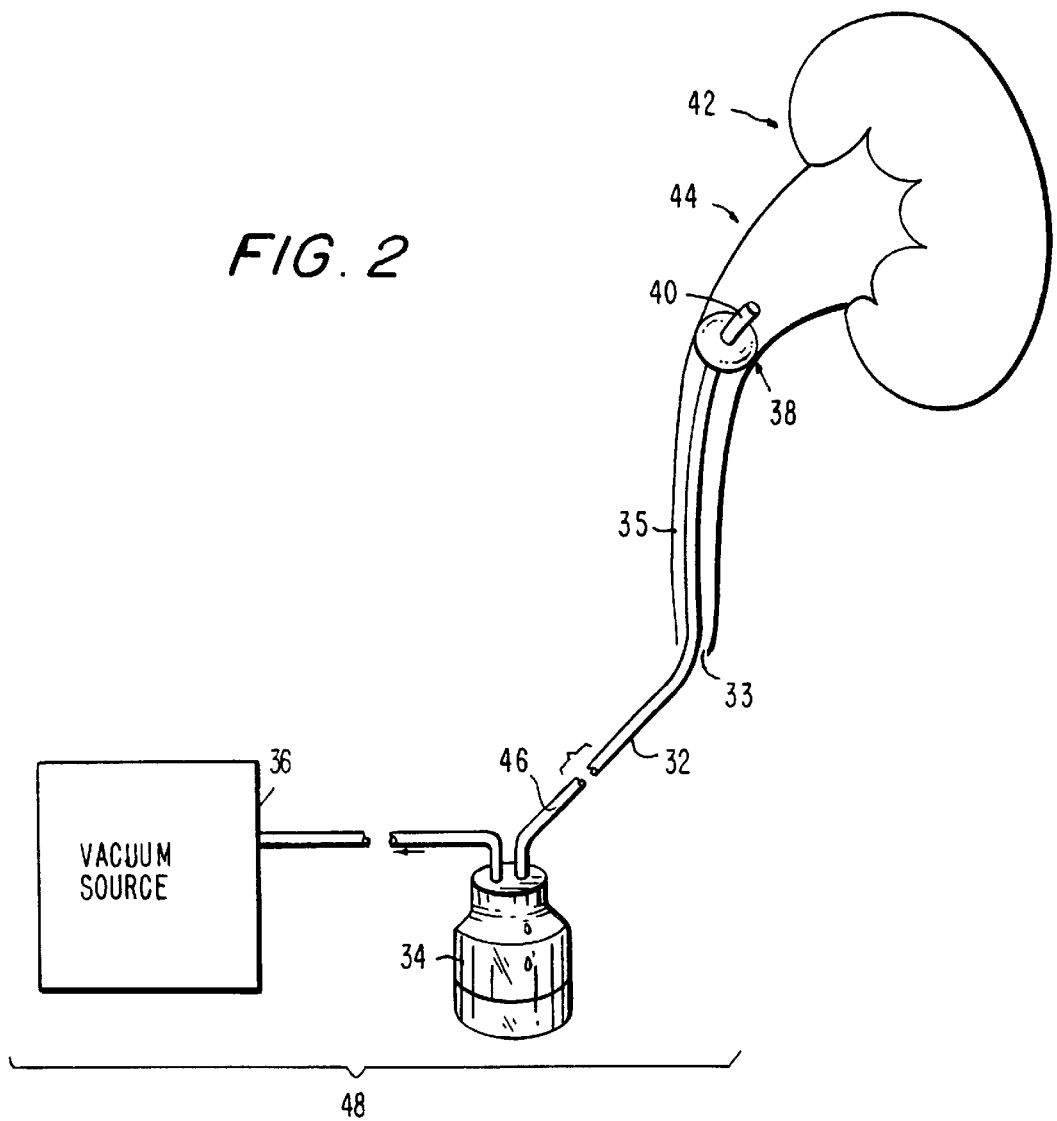
FIG. 2 is a perspective view of an apparatus which creates negative pressure according to the invention.

The present invention is directed to a method which reduces the pressure in the urinary outflow tract to increase the glomerular filtration and hence to increase kidney function as well. It is well known in renal physiology that the glomerular filtration rate (GFR) is a standard indicator of kidney function. As discussed above, the major determinant of GFR is the hydrostatic pressure gradient in the glomerulus. This gradient is the difference between the pressure within the afferent arteriole and the pressure within Bowman's capsule. Because Bowman's capsule is part of the renal tubule which is ultimately connected to the environment through the urinary outflow tract (which includes the ureter, bladder and urethra), the pressure within Bowman's capsule is essentially atmospheric pressure. According to the invention the pressure in the urinary outflow tract is reduced, which effectively increases the hydrostatic pressure gradient at the endothelial interface between the glomerular capillary and Bowman's capsule. Because reducing the pressure at the urinary outflow tract does not affect the colloid oncotic pressure within the capillary, this increase in the hydrostatic pressure gradient results in an increase in glomerular filtration.

The present invention provides a device which reduces the pressure of the urinary outflow tract. The device includes a catheter which may be inserted transurethrally and a pump which creates negative pressure. Any currently available catheter which has an inflatable balloon at its distal tip and a through lumen may be used. The catheter may be inserted and inflated anywhere in the urinary outflow tract. Preferably, the catheter is inserted and the inflatable balloom inflated in the ureter. Additionally, the device consists of a container where the cover has two ports, one connected to the suction or vacuum source and the other port connected to the catheter. The container collects any fluid that is obtained from the kidneys.

One embodiment of the present invention is illustrated in FIG. 2, where there is a ureteral catheter 32, a container 0.34 and a vacuum source 36. The ureteral catheter 32 has an inflatable balloon 38 at its distal tip. The ureteral catheter 32 is inserted transurethrally through the bladder and ureteral orifice 33, up the ureter 35 so that the distal portion 40 of the ureteral catheter 32 is positioned at the level of the renal pelvis 42 and the ureteropelvic junction 44. When the distal portion 40 is so positioned, the balloon 38 is inflated as shown in FIG. 2. The entire catheter is then moved proximally to a position where it completely occludes the ureter or ureteropelvic junction 44 as shown in FIG. 2. The proximal end 46 of the ureteral catheter 32 is then attached to a suction system 48 comprising a collection bottle 34 and a vacuum source 36, which delivers a negative pressure to the collecting system.

The ureteral catheter 32 necessary to perform this method is installed in a minimally invasive fashion transurethrally. This avoids the great morbidity associated with the percutaneous vascular catheters required to perform dialysis or hemoperfusion (i.e., bleeding, thrombosis). However, in another embodiment, the same catheter just described can be passed via a percutaneous nephrostomy route with the balloon occluding the tract traversed by the catheter.

While any catheter which completely occludes the lumen of the vessel in which it is lodged can be used according to the invention, one embodiment of the invention comprises a ureteral catheter as illustrated in FIGS. 3 and 3A. Catheter 65 has an inflatable balloon 70 at its distal section, which balloon 70 is shown inflated in FIG. 3 and uninflated in FIG. 3A. Port 76 at the proximal end of catheter 65 is in fluid connection with port 72 at the distal end of catheter, and inflation port 78 is in fluid communication with balloon 70 for inflation and deflation.

FIG. 4 illustrates a suction catheter 80 with a cage assembly 82 which provides a means to avoid clogging or plugging of catheter 80 due to suction and entrapment of the urinary collecting system mucosa in the suction hole or holes 84 of the catheter tip. The cage assembly 82 is composed of several, usually three to five, wire filaments 86 arranged to form a basket-like shape around the distal end 88 of catheter 80. Generally, wire filaments 86 are constructed and arranged on the distal end of the catheter so that they are capable of bowing to a sufficient degree so that catheter suction hole or holes 84 do not contact or entrap the urinary tract mucosa. A preferred embodiment of cage assembly 82 comprises a metal wire monofilament 86, although variations with plastic filament or bifilament are also acceptable.

A significant aspect of catheter 80 is that there are two tubes: one an inner catheter 90 having drainage holes 84 at its end which are in fluid communication with suction port 92, and an outer sheath 94 slideably arranged concentric to inner catheter 90. The respective ends of wire filaments 86 comprising cage assembly 82 are fastened to the distal ends of each of inner catheter 90 and outer sheath 94 such that cage assembly 82 may be either opened (FIG. 4) or closed (FIG. 5) dependent upon the positional relationship of inner catheter 90 to outer sheath 94. This positional relationship between inner catheter 90 and outer sheath 94 is easily affected by the clinician with a thumb loop 96 at the proximal end of inner catheter 90 and a finger grip 98 at the proximal end of outer sheath 94.

Also, drainage holes 84 of inner catheter 90 should be positioned such that they correspond to wire filaments 86 of the outer sheath 94. Thus, when the cage assembly 82 is opened (FIG. 4) and suction is applied to suction port 92, drainage holes 86 may remain unobstructed. Likewise, when cage assembly 82 is closed (FIG. 5), catheter 80 may be inserted or extracted with ease.

The method of the present invention has multiple clinical applications. For instance, this may serve as an alternative to temporary dialysis in patients with acute tubular necrosis or temporary fluid overload. In addition, increasing glomerular filtration may ultimately increase renal blood flow and act as a method of afterload reduction to the heart. Clinically, afterload is equivalent to the systemic blood pressure at aortic valve opening or shortly after peak systolic myocardial wall stress. Large afterload pressures are responsible for diseases such as enlarged heart and congestive heart failure. Thus, the present invention can be used to treat patients with enlarged hearts and congestive heart failure by reducing afterload pressures. In addition, improvement of renal blood flow can impact favorably upon cardiac hemodynamics (i.e., decrease afterload). This method can thus enhance or improve currently used methods of mechanically improving cardiac hemodynamics (i.e., intra-aortic balloon pumps) and fluid management in patients with renal failure or acute tubular necrosis (i.e., dialysis, hemoperfusion). Furthermore, this method is advantageous in terms of its practicality and morbidity compared to currently used methods.

The clinician can determine how much negative pressure to apply and the length of each treatment depending on the condition of the patient and the disease the patient is suffering from. A variable negative pressure may be applied to the renal collecting system in either a constant or pulsatile fashion. The negative pressure can also be applied to the urinary-collecting system with varying patterns. For example, the variation in the vacuum pressure correlates with specific portions of the cardiac cycle (i.e., systole).

Yet another aspect of this invention is the combination of reducing urinary outflow tract pressure and drug therapy to enhance glomerular filtration and hence kidney function. Any drugs which increase renal blood flow can be used including angiotensin converting enzyme inhibitors and anticatecholamines.

The container may be in any shape and be made of any material sturdy enough to withstand the negative pressures achieved by the pump.

The pump can be selected from any of the vacuum or suction pumps presently available and may run on any energy source.

The present invention provides a kit which contains the catheter, a container to collect the urine, and a pump. The kit should be small and light enough so that it is portable. The pump in the kit utilizes any source for energy. In one embodiment, batteries are used as the energy source so that the kit can be used anywhere.

The description above should not be construed as limiting the scope of the invention to the specific embodiments described which are provided merely as illustrations. The scope of the invention encompasses interchangeable substitutions known by those skilled in the art. Many other variations are possible. Thus the scope of the invention should be determined by the appended claim and their legal equivalents, rather than by the examples given.

What is claimed is:

1. An apparatus for use in increasing kidney function or treating renal failure or renal insufficiency comprising:

(a) a catheter with a proximal and a distal end having an inflatable balloon toward its distal end, said catheter having a distal tip extending beyond the balloon;

(b) a container having a first and a second port, wherein the first port is connected to the proximal end of the catheter; and (c) means for reducing the pressure within the urinary outflow tract, said means being connected to the second port.

2. The apparatus of claim 1, wherein the distal tip has at least one hole.

3. The apparatus of claim 2, wherein the catheter is further comprised of an inner and an outer catheter portion, wherein the inner portion extends distally of the distal end of the outer portion and said at least one hole are in the inner portion.

4. The apparatus of claim 3 further comprising a plurality of wire filaments connected to the distal end of the outer-portion and the distal end of the inner portion wherein said filaments bow outward when the inner portion slides proximally respective of the outer portion.

5. The apparatus of claim 4 further comprising a means at the proximal end of the catheter for sliding the inner portion and outer portion of the catheter with respect to each other.

* * * * *